United States Patent [19]

Yoshida et al.

[11] Patent Number: 4,713,403

[45] Date of Patent: Dec. 15, 1987

[54] DENTAL COMPOSITE RESIN COMPOSITION

[75] Inventors: Bunsaku Yoshida, Ichikawa; Kentaro Tomioka, Chofu, both of Japan

[73] Assignee: G-C Dental Industrial Corporation, Tokyo, Japan

[21] Appl. No.: 843,195

[22] Filed: Mar. 24, 1986

[30] Foreign Application Priority Data

Apr. 2, 1985 [JP] Japan ............................... 60-68533

[51] Int. Cl.[4] .............................................. A61K 6/08
[52] U.S. Cl. ...................................... 523/115; 523/116; 524/403; 524/413; 524/440
[58] Field of Search ............... 523/115, 116; 524/403, 524/440, 413

[56] References Cited

U.S. PATENT DOCUMENTS

| | | | |
|---|---|---|---|
| 3,973,972 | 8/1976 | Muller | 523/116 |
| 4,001,939 | 1/1977 | Gross | 523/115 |
| 4,499,251 | 2/1985 | Omura et al. | 523/115 |

*Primary Examiner*—Morton Foelak
*Assistant Examiner*—Kriellion Morgan
*Attorney, Agent, or Firm*—Oblon, Fisher, Spivak, McClelland & Maier

[57] ABSTRACT

A dental composite resin composition is disclosed, which comprises as main components a polymerizable monomer, an inorganic and/or organic filler, a gold powder and/or a gold-color alloy powder, and a polymerization catalyst. The dental composite resin composition of the present invention is useful as a filling material for repairing a tooth cavity, which has a gold-color luster and exhibits an excellent abrasion resistance as well as an excellent x-ray contrast.

14 Claims, No Drawings

DENTAL COMPOSITE RESIN COMPOSITION

FIELD OF THE INVENTION

The present invention relates to a dental composite resin composition useful as a filling material for repairing a tooth cavity.

BACKGROUND OF THE INVENTION

As a filling material used in the dentistry, a dental amalgam which is prepared by mixing a dental amalgam alloy powder and mercury has hitherto been mainly employed. However, since this dental amalgam uses mercury which is harmful to human bodies and likely causing an environmental pollution, in recent years a dental composite resin composition has become widely used as a replacement of the dental amalgam, in view of the safety.

Such a dental composite resin composition is generally composed of a polymerizable monomer, an inorganic filler and/or an organic filler, a polymerization catalyst, a pigment, and a stabilizer and is usually in the form of two types of pastes in which one paste is incorporated with peroxide and the other paste is incorporated with amines or sulfinic acids. These two pastes are mixed at the time of use and then polymerized.

This dental composite resin composition is generally classified, depending upon the type of the filler used, into a conventional type composite resin having an irregular particle sized filler of about 1~50 μm, such as silica, quartz, barium glass, lithium aluminum silicate, and ceramics, and a MFR (microparticle filled resin) type composite resin having superfine sized silica filler of 0.005~0.04 μm.

However, the above-described dental composite resin composition has such a drawback in abrasion resistance that its cured material is readily abraded by mastication of foods as compared with the dental amalgam. In particular, the cured conventional type composite resin composition has a drawback that after abrasion in an oral cavity, its surface becomes rough. In order to solve such a drawback that the surface becomes rough, MFR has been developed, but its abrasion resistance is rather reduced. Further, while the X-ray contrast is a very useful property in diagnosis by a dentist, when a compound such as barium, lead, tungsten, or zirconium is added as a X-ray contrast medium to the dental composite resin composition, the mechanical properties are decreased and the color tone is deteriorated, and hence, it is difficult to impart a satisfactory X-ray contrast.

In order to overcome the drawbacks of the above-described dental composite resin composition, the present inventors have made extensive investigations and found that it is effective to add a platinum-color element powder and/or a platinum-color alloy powder to the dental composite resin composition.

SUMMARY OF THE INVENTION

An object of the present invention is to provide a dental composite resin composition comprising as main components a polymerizable monomer, an inorganic filler and/or an organic filler, a gold powder and/or a gold-color alloy powder, and a polymerization catalyst.

DETAILED DESCRIPTION OF THE INVENTION

The present invention relates to a dental composite resin composition which contains a gold powder and/or a gold-color alloy powder. The dental composite resin composition of the present invention is not only excellent in aesthetic properties for the dental use but also quite effective as a means for improving the X-ray contrast because of containing the gold powder and/or gold-color alloy powder. Further, it can improve the surface smoothness and the surface hardness without reducing the abrasion resistance of the cured dental composite resin. It is considered that this is caused by the matter that the metal powder present in the surface layer is work hardening by polishing or mastication over a long period of time to thereby strengthen the matrix.

Examples of the gold powder or gold-color alloy powder which can be used in the present invention include gold powder, gold base alloy powder, Cu-Zn base alloy powder, Cu-Al base alloy powder, In-Pd base alloy powder, Zn-Pd base alloy powder, TiN powder, etc. Among them, the gold powders, and gold base alloy powders, are preferred because they are free from tarnish in the oral cavity and are excellent in X-ray contrast.

A suitable amount of the gold powder and/or gold-color alloy powder which is incorporated into the dental composite resin composition is in the range of from 1 to 60% by weight. If the amount is too large, the physical properties tend to be decreased, whereas if it is too small, the desired effects cannot be exhibited satisfactorily.

A suitable particle size of the gold powder or gold-color alloy powder which is used is 50 μm or less and preferably 20 μm or less. If the particle size is too large, not only the workability is deteriorated but also a surface of the cured material tends to become rough.

With respect to the shape of particles of the gold powder or gold-color alloy powder, there is no particular restriction, but thin foil-like or flake-like ones are preferred for the appearance of metallic color.

Though the gold powder or gold-color alloy powder can be incorporated as it stands, it is preferred to do the surface treatment with a silane coupling agent. Examples of the silane coupling agent which can be used include vinyl trichlorosilane, vinyl triethoxysilane, vinyl trimethoxysilane, vinyl tris(β-methoxyethoxy)silane, and γ-methacryloxypropyl trimethoxysilane The polymerizable monomer which is used in the present invention may be either a monofunctional monomer or a polyfunctional monomer.

Examples of the monofunctional monomer include methyl acrylate, methyl methacrylate, ethyl acrylate, ethyl methacrylate, butyl acrylate, butyl methacrylate, acryl acrylate, acryl methacrylate, hydroxyethyl acrylate, hydroxyethyl methacrylate, methoxyethyl acrylate, and methoxyethyl methacrylate. Examples of the polyfunctional monomer include bifunctional aliphatic acrylates, bifunctional aliphatic methacrylates, bifunctional aromatic acrylates, bifunctional aromatic methacrylates, trifunctional aliphatic acrylates, trifunctional aliphatic methacrylates, tetrafunctional acrylates, and tetrafunctional methacrylates, such as triethylene glycol diacrylate, triethylene glycol dimethacrylate, 2,2-bis(4-methacryloxyphenyl)propane, 2,2-bis(4-methacryloxyethoxyphenyl)propane, 2,2-bis(4-methacryloxypolyethoxyphenyl]propane, 2,2-bis[4-(3-methacryloxy-2-hydroxypropoxy)-phenyl]propane, di(methacryloxyethyl) trimethylhexamethylene diurethane, tetramethylolmethane tetraacrylate, and tetramethylolmethane tetramethacrylate. These polymerizable monomers can be used alone or in admixture of two or more thereof.

As the filler which is used in the present invention, inorganic fillers such as silica powder, quartz, glass beads, aluminum oxide, and ceramics are usually used. A suitable particle size of the inorganic filler is generally 50 μm or less, but those fine particles having a particle diameter of 10 μm or less are preferred from the standpoint of smoothness of the surface. These particles can be, as a matter of course, used in combination. Further, though the inorganic filler can be added alone, it is preferred to previously subject to surface treatment with a silane coupling agent. Examples of the silane coupling agent which can be used include vinyl trichlorosilane, vinyl triethoxysilane, vinyl trimethoxysilane, vinyl tris(β-methoxyethoxy)silane, and γ-methacryloxypropyl trimethoxysilane. Moreover, an organic filler prepared by mixing superfinely divided silica and the polymerizable monomer, polymerizing and curing it, and then pulverizing the polymer can also be used as the filler.

A suitable amount of the filler which is incorporated into the dental composite resin composition is usually in the range of about 20~80% by weight.

As the polymerization catalyst which is used in the present invention, known catalysts such as, for example, a so-called redox catalyst, e.g., a combination of amines and peroxides or a combination of sulfinic acids and peroxides, can be used. Examples of the peroxide include diacyl peroxide group such as benzoyl peroxide, p-chlorobenzoyl peroxide, 2,4-dichlorobenzoyl peroxide, acetyl peroxide, and lauroyl peroxide; hydroperoxide group such as t-butyl hydroperoxide, cumene hydroperoxide, and 2,5-dimethylhexane 2,5-dihydroperoxide; ketone peroxide group such as methyl ethyl ketone peroxide; and peroxycarbonate group such as t-butyl peroxybenzoate.

Examples of the amine which is combined with the above-described peroxide include N,N-bis-(2-hydroxyethyl)4-methylaniline, N,N-bis-(2-hydroxyethyl)-3,4-dimethylaniline, N,N-bis-(2-hydroxyethyl)-3,5-dimethylaniline, N-methyl-N-(2-hydroxyethyl)-4-methylaniline, 4-methylaniline, N,N-dimethyl-p-toluidine, N,N-dimethylaniline, and triethanolamine. Examples of the sulfinic acid which is combined with the peroxide include p-toluenesulfinic acid, benzenesulfinic acid, and salts thereof. Further, examples of other material which is combined with the peroxide include cobalt naphthenate, cobalt octanate, trimethyl barbituric acid, and a trialkyl boron. In the case that the polymerization catalyst is used, a mixture of the above-described polymerizable monomer and filler is divided into two parts, the amine or sulfinic acid is incorporated into one part whereas the peroxide is incorporated into the other part, and the both parts are mixed at the time of use.

If desired, known pigments, stabilizers and the like can be added to the dental composite resin composition according to the present invention. Examples of stabilizer include hydroquinone, hydroquinone monomethyl ether, t-butyl paracresol and hydroxy methoxybenzophenone.

A filling material using the dental composite resin composition comprising the above-described components according to the present invention is markedly easy in workability as compared with an inlay by casting of a metal, is inexpensive in cost, and is light in weight. Further, it exhibits a gold color in external appearance likewise the inlay by a gold alloy and is free from tarnish even after the use in an oral cavity over a long period of time, and hence, it gives to patients confidence as in an inlay by gold alloy. Still further, the dental composite resin composition of the present invention has a smooth surface and an excellent surface hardness in comparable to the conventional ones and is provided with usuful X-ray contrast in diagnosis by a dentist, and hence, it possesses suitable properties as the dental composite resin composition.

The present invention is described in more detail with reference to the following examples.

EXAMPLES

Pastes A to P each having the following composition were prepared.

Paste A 2,2-Bis[4-(3-methacryloxy-2-hydroxypropyl)-phenyl]propane: 15.5 parts by weight Triethylene glycol dimethacrylate: 15.5 parts by weight Quartz treated with γ-methacryloxypropyl trimethoxysilane (50 μm or less): 67.5 parts by weight Benzoyl peroxide: 1.5 parts by weight Hydroquinone monomethyl ether: 0.01 part by weight Paste A'

2,2-Bis[4-(3-methacryloxy-2-hydroxypropyl)-pheny]propane: 15.5 parts by weight

Triethylene glycol dimethacrylate: 15.5 parts by weight

Quartz treated with γ-methacryloxypropyl trimethoxysilane (50 μm or less): 67.0 parts by weight N,N-Dimethyl-p-toluidine: 2.0 parts by weight Hydroquinone monomethyl ether: 0.01 part by weight Paste B The above paste A: 50 parts by weight. A gold powder (20 μm or less): 50 parts by weight.

Paste B'

The above paste A': 50 parts by weight. A gold powder (20 μm or less): 50 parts by weight.

Paste C

The above paste A: 80 parts by weight. A gold powder (20 μm or less): 20 parts by weight.

Paste C'

The above paste A': 80 parts by weight. A gold powder (20 μm or less): 20 parts by weight.

Paste D

The above paste A: 85 parts by weight. A powder (20 μm or less) of a gold base alloy (75 wt % Au-12.5 wt % Ag12.5 wt % Cu) treated with γ-methacryloxypropyl trimethoxysilane: 15 parts by weight.

Paste D'

The above paste A': 85 parts by weight. A powder (20 μm or less) of a gold base alloy (75 wt % Au-12.5 wt % Ag12.5 wt % Cu) treated with γ-methacryloxypropyl trimethoxysilane: 15 parts by weight.

Paste E

The above paste A: 55 parts by weight. A powder (44 μm or less) of a gold base alloy (60 wt % Au-20 wt % Cu18 wt % Ag-2 wt % Zn) treated with vinyl trimethoxysilane: 45 parts by weight.

Paste E'

The above paste A': 55 parts by weight. A powder (44 μm or less) of a gold base alloy (60 wt % Au-20 wt % Cu18 wt % Ag-2 wt % Zn) treated with vinyl trimethoxysilane: 45 parts by weight.

Paste F

The above paste A: 65 parts by weight A gold powder (50 μm or less) treated with γ-methacryloxypropyl trimethoxysilane: 35 parts by weight.

Paste F'

The above paste A': 65 parts by weight. A gold powder (50 μm or less) treated with γ-methacryloxypropyl trimethoxysilane: 35 parts by weight.

Paste G

Di(methacryloxyethyl) trimethylhexamethylene diurethane: 24.0 parts by weight

Triethylene glycol dimethacrylate: 16.0 parts by weight

Organic filler (50 μm or less) which was prepared by block polymerizing a composition of 50 parts by weight of finely divided silica (particle size: 50 m μm or less), 30 parts by weight of di(methacryloxyethyl) trimethylhexamethylene diurethane, 20 parts by weight of triethylene glycol dimethacrylate and 1 part by weight of benzoyl peroxide and pulverizing the polymer by means of a mill to 50 μm or less: 58.5 parts by weight Benzoyl peroxide: 1.5 parts by weight Hydroquinone monomethyl ether: 0.01 part by weight

Paste G'

Di(methacryloxyethyl) trimethylhexamethylene diurethane: 24.0 parts by weight

Triethylene glycol dimethacrylate: 16.0 parts by weight

Organic filler (50 μm or less) which was prepared by block polymerizing a composition of 50 parts by weight of finely divided silica (particle size: 50 m μm or less), 30 parts by weight of di(methacryloxyethyl) trimethylhexamethylene diurethane, 20 parts by weight of triethylene glycol dimethacrylate and 1 part by weight of benzoyl peroxide and pulverizing the polymer by means of a mill to 50 μm or less: 58.0 parts by weight N,N-Dimethyl-p-toluidine: 2.0 parts by weight Hydroquinone monomethyl ether: 0.01 part by weight

Paste H

The above paste G: 45 parts by weight. A gold powder (20 μm or less) treated with γ-methacryloxypropyl trimethoxysilane: 55 parts by weight.

Paste H'

The above paste G': 45 parts by weight. A gold powder (20 μm or less) treated with γ-methacryloxypropyl trimethoxysilane: 55 parts by weight.

Paste I

The above paste G: 95 parts by weight. A powder (20 μm or less) of a In-Pd alloy (50 wt % In-50 wt % Pd): 5 parts by weight.

Paste I'

The above paste G': 95 parts by weight. A powder (20 μm or less) of a In-Pd alloy (50 wt % In-50 wt % Pd): 5 parts by weight.

Paste J

The above paste G: 70 parts by weight. A gold powder (20 μm or less) treated with γ-methacryloxypropyl trimethoxysilane: 30 parts by weight.

Paste J'

The above paste G':70 parts by weight. A gold powder (20 μm or less) treated with γ-methacryloxypropyl trimethoxysilane: 30 parts by weight.

Paste K

The above paste G:90 parts by weight. A gold powder (20 μm or less) treated with vinyl trimethoxysilane: 10 parts by weight.

Paste K'

The above paste G':90 parts by weight. A gold powder (20 μm or less) treated with vinyl trimethoxysilane: 10 parts by weight.

Paste L

Di(methacryloxyethyl) trimethylhexamethylene diurethane: 18.0 parts by weight

Triethylene glycol dimethacrylate: 12.0 parts by weight

Organic filler (50 μm or less) which was prepared by block polymerizing a composition of 50 parts by weight of finely divided silica (particle size: 50 m μm or less), 30 parts by weight of di(methacryloxyethyl) trimethylhexamethylene diurethane, 20 parts by weight of triethylene glycol dimethacrylate and 1 part by weight of benzoyl peroxide and pulverizing the polymer by means of a mill to 50 μm or less: 49.1 parts by weight Glass beads (50 μm or less) treated with vinyl trimethoxysilane: 19.5 parts by weight Benzoyl peroxide: 1.5 parts by weight Hydroquinone monomethyl ether: 0.01 part by weight

Paste L'

Di(methacryloxyethyl) trimethylhexamethylene diurethane: 18.0 parts by weight

Triethylene glycol dimethacrylate: 12.0 parts by weight

Organic filler (50 μm or less) which was prepared by block polymerizing a composition of 50 parts by weight of finely divided silica (particle size: 50 m μm or less), 30 parts by weight of di(methacryloxyethyl) trimethylhexamethylene diurethane, 20 parts by weight of triethylene glycol dimethacrylate and 1 part by weight of benzoyl peroxide and pulverizing the polymer by means of a mill to 50 μm or less: 48.5 parts by weight Glass beads (50 μm or less) treated with vinyl trimethoxysilane: 19.5 parts by weight N,N-dimethyl-p-toludine: 2.0 parts by weight Hydroquinone monomethyl ether: 0.01 part by weight

Paste M

The above paste L: 60 parts by weight. A gold powder (20 μm or less) treated with vinyl trimethoxysilane: 40 parts by weight.

Paste M'

The above paste L': 60 parts by weight. A gold powder (20 μm or less) treated with vinyl trimethoxysilane: 40 parts by weight.

Paste N

The above paste L: 60 parts by weight. A powder (44 μm or less) of a gold base alloy (90 wt % Au-10 wt % Ag): 40 parts by weight.

Paste N'

The above paste L': 60 parts by weight. A powder (44 μm or less) of a gold base alloy (90 wt % Au-10 wt % Ag): 40 parts by weight.

Paste O

The above paste L: 90 parts by weight. A gold powder (20 μm or less) treated with vinyl trimethoxysilane: 10 parts by weight.

Paste O'

The above paste L': 90 parts by weight. A gold powder (20 μm or less) treated with vinyl trimethoxysilane: 10 parts by weight.

Paste P

The above paste L: 99.5 parts by weight. A powder (20 μm or less) of a TiN treated with vinyl trimethoxysilane: 0.5 parts by weight.

Each of the above-described pastes was prepared by mixing, and dissolving the polymerizable monomer, dissolving the polymerization catalyst for the polymerizable monomer as well as the stabilizer, and then adding thereto the filler and the gold powder and/or gold-color alloy powder, followed by degassing and kneading. Thereafter, based on the combination of Examples 1 to 20 and Comparative Examples 1 to 4 shown in the table below, the same amount of each of the pastes was taken and mixed. As the result, all of the pastes were cured within 8 minutes.

Further, in order to evaluate the properties of the cured material, a disc-like cured material having a size of 10 mmφ×5 mm was prepared by using the same amount of each of the pastes based on the combination of each of Examples 1 to 20 and Comparative Examples 1 to 4, and the measurement of surface hardness, the measurement of wear depth by the abrasion test, and the X-ray contrast were evaluated.

In the above evaluation, the measurement of surface hardness was carried out by measuring the Knoop hardness at a load of 200 g for 30 seconds.

The measurement of wear depth by the abrasion test was carried out by the toothbrush test by 50,000 times using a commercially available toothbrush and tooth paste.

The X-ray contrast was carried out by placing each cured material on an X-ray film, irradiating it with X-rays, and then developing the X-ray film.

The results obtained are shown in the table below.

| Example and Comparative Example No.* | Hardness of Surface (Hk) | Wear Depth by Abrasion Test (cm) | X-Ray Contrast |
|---|---|---|---|
| Ex. 1 | 82 | $1.55 \times 10^{-5}$ | Good |
| Ex. 2 | 77 | $1.66 \times 10^{-5}$ | " |
| Ex. 3 | 75 | $1.77 \times 10^{-5}$ | " |
| Ex. 4 | 76 | $1.73 \times 10^{-5}$ | " |
| Ex. 5 | 82 | $1.56 \times 10^{-5}$ | " |
| Ex. 6 | 80 | $1.60 \times 10^{-5}$ | " |
| Ex. 7 | 73 | $1.79 \times 10^{-5}$ | " |
| Ex. 8 | 77 | $1.67 \times 10^{-5}$ | " |
| Ex. 9 | 52 | $3.11 \times 10^{-5}$ | " |
| Ex. 10 | 41 | $3.57 \times 10^{-5}$ | " |
| Ex. 11 | 48 | $3.29 \times 10^{-5}$ | " |
| Ex. 12 | 43 | $3.50 \times 10^{-5}$ | " |
| Ex. 13 | 41 | $3.55 \times 10^{-5}$ | " |
| Ex. 14 | 50 | $3.31 \times 10^{-5}$ | " |
| Ex. 15 | 77 | $2.50 \times 10^{-5}$ | " |
| Ex. 16 | 78 | $2.52 \times 10^{-5}$ | " |
| Ex. 17 | 78 | $2.50 \times 10^{-5}$ | " |
| Ex. 18 | 66 | $2.92 \times 10^{-5}$ | " |
| Ex. 19 | 70 | $2.76 \times 10^{-5}$ | " |
| Ex. 20 | 63 | $3.02 \times 10^{-5}$ | " |
| Com. Ex. 1 | 68 | $1.87 \times 10^{-5}$ | Nil |
| Com. Ex. 2 | 31 | $4.08 \times 10^{-5}$ | " |
| Com. Ex. 3 | 57 | $3.71 \times 10^{-5}$ | " |
| Com. Ex. 4 | 57 | $3.69 \times 10^{-5}$ | Weak |

Ex. 1: cured material of paste B and paste B'
Ex. 2: cured material of paste C and paste C'
Ex. 3: cured material of paste A and paste C'
Ex. 4: cured material of paste D and paste D'
Ex. 5: cured material of paste E and paste E'
Ex. 6: cured material of paste F and paste F'
Ex. 7: cured material of paste D and paste A'
Ex. 8: cured material of paste D and paste C'
Ex. 9: cured material of paste H and paste H'
Ex. 10: cured material of paste I and paste I'
Ex. 11: cured material of paste J and paste J'
Ex. 12: cured material of paste K and paste K'
Ex. 13: cured material of paste K and paste G'
Ex. 14: cured material of paste H and paste I'
Ex. 15: cured material of paste M and paste M'
Ex. 16: cured material of paste N and paste N'
Ex. 17: cured material of paste M and paste N'
Ex. 18: cured material of paste O and paste O'
Ex. 19: cured material of paste N and paste O'
Ex. 20: cured material of paste P and paste O'
Com. Ex. 1: cured material of paste A and paste A'
Com. Ex. 2: cured material of paste G and paste G'
Com. Ex. 3: cured material of paste L and paste L'
Com. Ex. 4: cured material of paste P and paste L'

It was confirmed from the comparison between Examples 1 to 8 and Comparative Example 1, the comparison between Examples 9 to 14 and Comparative Example 2, and the comparison between Examples 15 to 20 and Comparative Example 3 that the dental composite resin composition into which a gold powder and/or a gold-color alloy powder is incorporated according to the present invention exhibits excellent properties in surface hardness, abrasion resistance and X-ray contrast. Further, in Comparative Example 4, because of shortness of the gold-color alloy powder, substantial improvements in surface hardness and abrasion resistance were not observed, and the color tone of the cured material was not satisfactory in gold color.

A filling material prepared by using the dental composite resin composition according to the present invention had a gold-color luster likewise an inlay by gold alloy and kept the gold-color luster without causing any tarnish even after the lapse of 2 years in an oral cavity, and was not substantially observed to be abraded, whereby it showed excellent clinical results.

While the invention has been described in detail and with reference to specific embodiments thereof, it will be apparent to one skilled in the art that various changes and modifications can be made therein without departing from the spirit and scope thereof.

What is claimed is:

1. A dental composite resin composition comprising as main components a polymerizable monomer, which is a monofunctional or polyfunctional acrylate or methacrylate, an inorganic filler and/or an organic filler, a gold powder and/or a gold-color alloy powder having a gold-color luster, and a redox polymerization catalyst.

2. A dental composite resin composition as claimed in claim 1, wherein the content of said gold powder and/or gold-color alloy powder is in the range of from 1 to 60% by weight.

3. A dental composite resin composition as claimed in claim 1, wherein the particle size of said gold powder and/or gold-color alloy powder is 50 $\mu$m or less.

4. A dental composite resin composition as claimed in claim 2, wherein the particle size of said gold powder and/or gold-color alloy powder is 50 $\mu$m or less.

5. A dental composite resin composition as claimed in claim 1, wherein said gold powder and/or gold-color alloy powder is subjected to surface treatment with a silane coupling agent.

6. A dental composite resin composition as claimed in claim 2, wherein said gold powder and/or gold-color alloy powder is subjected to surface treatment with a silane coupling agent.

7. A dental composite resin composition as claimed in claim 3, wherein said gold powder and/or gold-color alloy powder is subjected to surface treatment with a silane coupling agent.

8. A dental composite resin composition as claimed in claim 4, wherein said gold powder and/or gold-color alloy powder is subjected to surface treatment with a silane coupling agent.

9. A dental composite resin composition as claimed in claim 1, wherein said gold powder and/or gold-color alloy powder is selected from the group consisting of gold powder, gold base alloy powder, Cu-Zn base alloy powder, Cu-Al base alloy powder, In-Pd base alloy powder, Zn-Pd base alloy powder and TiN powder.

10. A dental composite resin composition as claimed in claim 9, wherein the content of said gold powder and/or gold-color alloy powder is in the range of from 1 to 60% by weight.

11. A dental composite resin composition as claimed in claim 9, wherein the particle size of said gold powder and/or gold-color alloy powder is 50 $\mu$m or less.

12. A dental composite resin composition as claimed in claim 9, wherein said gold powder and/or gold-color alloy powder is subjected to surface treatment with a silane coupling agent.

13. A dental composite resin composition as claimed in claim 10, wherein said gold powder and/or gold-color alloy powder is subjected to surface treatment with a silane coupling agent.

14. A dental composite resin composition as claimed in claim 11, wherein said gold powder and/or gold-color alloy powder is subjected to surface treatment with a silane coupling agent.

* * * * *